United States Patent [19]

Perez

[11] 4,444,577
[45] Apr. 24, 1984

[54] CRYOGENIC GAS PROCESSING

[75] Inventor: Ethelwolbo P. Perez, London, England

[73] Assignee: Phillips Petroleum Company, Bartlesville, Okla.

[21] Appl. No.: 416,202

[22] Filed: Sep. 9, 1982

[51] Int. Cl.³ .............................................. F25J 3/02
[52] U.S. Cl. ......................................... 62/30; 62/31; 62/34; 62/39
[58] Field of Search ...................... 62/38, 39, 9, 11, 23, 62/24, 27, 29, 31, 32, 33, 34, 42, 30; 55/27, 68

[56] References Cited

U.S. PATENT DOCUMENTS

| | | | |
|---|---|---|---|
| 3,702,541 | 11/1972 | Randall et al. | 62/39 |
| 4,040,806 | 8/1977 | Kennedy | 62/39 |
| 4,274,850 | 6/1981 | Becker | 62/38 |

*Primary Examiner*—Frank Sever

[57] ABSTRACT

Higher boiling constituents are separated from a normally gaseous feed mixture, predominating in lower boiling constituents and containing significant amounts of such higher boiling constituents, such as natural gas by fractionally distilling a feed mixture having a temperature substantially below atmospheric temperature at a pressure substantially above atmospheric pressure at which temperature and pressure the feed mixture comprises both vapor and liquid phases to produce a first vapor phase substantially enriched in lower boiling constituents and a first liquid phase substantially enriched in higher boiling constituents, expanding at least a part of the first vapor phase to reduce the pressure and temperature and produce an expanded fluid stream comprising a second vapor phase and a second liquid phase, separating the second vapor phase from the second liquid phase, recycling the second liquid phase to the fractional distillation step as a reflux, recovering the second vapor phase as a product and recovering the first liquid phase as a product. In another embodiment, at least a part of the feed mixture is expanded prior to fractional distillation. In other embodiments, the feed mixture is separated into a vapor phase and a liquid phase and at least a part of the vapor phase is expanded and/or the feed mixture is first cooled by indirect heat exchange with the second vapor phase prior to recovery of the latter as a product.

25 Claims, 1 Drawing Figure

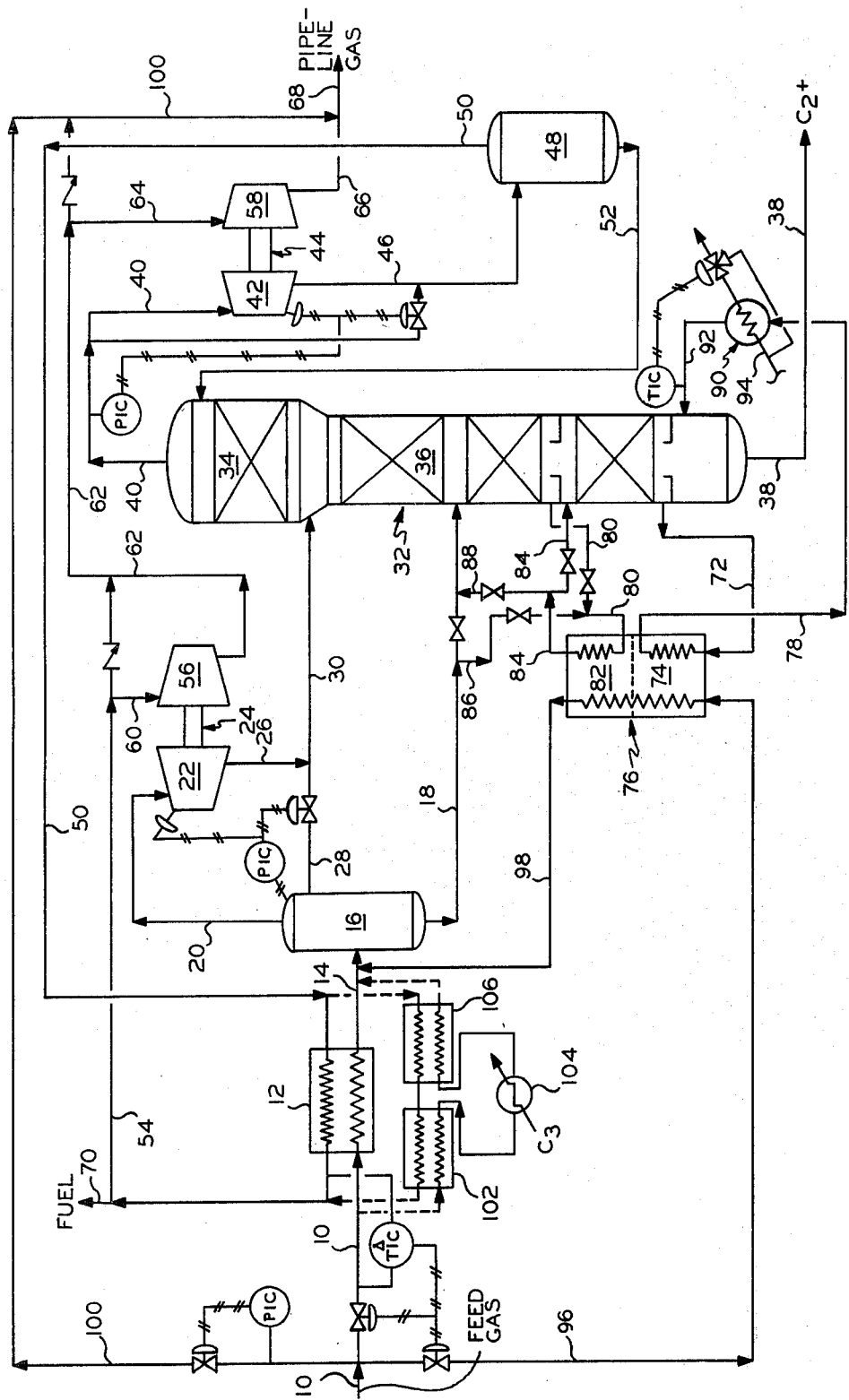

CRYOGENIC GAS PROCESSING

BACKGROUND OF THE INVENTION

The present invention relates to separating high boiling constituents from a gaseous feed mixture containing high and low boiling constituents. More specifically, the present invention relates to the separation of high molecular weight hydrocarbons from a natural gas feed containing high and low molecular weight hydrocarbons.

The problems associated with prior art systems for separating higher and lower boiling constituents of mixture thereof is best illustrated by the separation of high and low boiling hydrocarbons of natural gas. Natural gas, as it is received from a subsurface formation, generally is not suitable for direct use without some processing, since it contains $CO_2$, $H_2S$ and water as contaminants. The processing operations carried out in a natural gas plant are to first remove $CO_2$ and then pass the gas through a dehydration system to remove water. The amount of water $CO_2$ and $H_2S$ contained in the gas vary considerably but, in any event most gases contain significant amounts of these contaminants. In cryogenic separation techniques, the water and $CO_2$ are removed prior to cryogenic separation and the $H_2S$ is removed during the cryogenic separation, usually by means of fractional distillation. The preliminary dehydration and $CO_2$ removal, of course, add to the cost of the operation. Therefore, it would be highly desirable if one of these operations, for example, the removal of $CO_2$, could be eliminated. After removal of water, $CO_2$ and $H_2S$, the resulting gas can then be used as a fuel. However, such gases generally contain varying but significant amounts of higher molecular weight components, such as ethane and, to a lesser extent, propane, butanes and higher molecular weight hydrocarbons. The ethane and higher molecular weight hydrocarbons contribute relatively little heating value to the natural gas and accordingly, these materials have a significantly greater value as chemical feedstocks than as a fuel.

The natural gas feed to a natural gas plant will generally be near atmospheric temperature and at an elevated pressure substantially above atmospheric pressure, either as it is produced from the gas formation or as a result of the compression thereof. Therefore, it has long been known to separate ethane and higher molecular weight hydrocarbons from methane by a combination of plural cooling stages and at least one expansion stage and separating the cooled and expanded fluid by fractional distillation in a "demethanizer" to produce a vapor stream substantially higher in methane contact than the original gas and a liquid stream substantially higher in ethane and higher hydrocarbons than the original gas. An effective system of this type is shown, for example, in U.S. Pat. No. 4,322,225. The system of this patent utilizes two expansion stages in series, which is generally considered more efficient than a single stage system. However, even multiple stage expansion systems are inefficient in the removal of ethane and higher hydrocarbons. In addition, since the expansion stage or stages are connected to and drive compression stages, utilized for various purposes within the natural gas processing system, the energy generated by the expanders is usually inadequate to handle all of the pressure requirements and the refrigeration needs of the overall plant. Consequently, it would also be highly desirable, from an energy saving standpoint, to increase the power output of the expanders. Also, the demethanizer either must be rather large and/or a given size demethanizer is limited in its throughput capacity. Finally, the amounts of ethane retained in the separated methane stream is often higher than desirable.

SUMMARY OF THE INVENTION

It is therefore an object of the present invention to overcome the above-mentioned and other problems of the prior art. Another object of the present invention is to provide an improved method for separating higher boiling constituents from a normally gaseous feed mixture, predominating in lower boiling constituents and containing significant amounts of said higher boiling constituents. Yet another object of the present invention is to provide an improved method for separating ethane and higher molecular weight hydrocarbons from a natural gas, predominating in methane and containing significant amounts of said ethane and higher molecular weight hydrocarbons. A further object of the present inventon is to provide an improved method for separating high boiling constituents from a normally gaseous feed mixture, predominating in lower boiling constituents and containing significant amounts of said higher boiling constituents by cryogenic means. Another and further object of the present invention is to provide an improved method for separating higher boiling constituents from a normally gaseous feed mixture, predominating in lower boiling constituents and containing significant amounts of said higher boiling constituents by a combination of cooling and expansion. Another and further object of the present invention is to provide an improved method and apparatus for separating higher boiling constituents from a normally gaseous feed mixture, predominating in lower boiling constituents and containing significant amounts of said higher boiling constituents by a combination of cooling, expansion and fractional distillation. Another and further object of the present invention is to provide an improved method for separating ethane and higher molecular weight hydrocarbons from natural gas containing predominant amounts of methane and significant amounts of said ethane and higher molecular weight hydrocarbons, wherein the volume of ethane and higher molecular weight hydrocarbons, thus removed, is significantly increased. A still further object of the present invention is to provide an improved method for separating ethane and higher molecular weight hydrocarbons from a natural gas, predominating in methane and containing significant amounts of said ethane in higher molecular weight hydrocarbons and carbon dioxide. Yet another object of the present invention is to provide an improved method for separating higher molecular weight constituents from a normally gaseous feed mixture, predominating in lower boiling constituents, and containing significant amounts of said higher boiling constituents by a combination of fractional distillation and at least one expansion step. Another object of the present invention is to provide an improved method for the separation of higher boiling constituents from a normally gaseous feed mixture, predominating in lower boiling constituents and containing significant amounts of said higher boiling constituents, by the combination of fractional distillation and at least one expansion stage, wherein the energy produced by the expansion stage is substantially increased. These and other objects of the present invention will be apparent from the following description.

In accordance with the present invention, higher boiling constituents are separated from a normally gaseous feed mixture, predominating in lower boiling constituents and containing significant amounts of such higher boiling constituents, by fractionally distilling a feed mixture having a temperature substantially below atmospheric temperature at a pressure substantially above atmospheric pressure, at which temperature and pressure the feed mixture comprises both vapor and liquid phases, to produce a first vapor phase substantially enriched in lower boiling constituents and a first liquid phase substantially enriched in higher boiling constituents, expanding, at least a part of, the first vapor phase to reduce the pressure and temperature and produce an expanded fluid stream comprising a second vapor phase and a second liquid phase, separating the second vapor phase from the second liquid phase, recycling the second liquid phase to the fractional distillation step, as a reflux, recovering the second vapor phase as a product and recovering the first liquid phase as a product. In another embodiment, at least a part of the feed mixture is expanded prior to fractional distillation. In other embodiments, the feed mixture is separated into a vapor phase and a liquid phase and at least part of the vapor phase is expanded and/or the feed mixture is first cooled by indirect heat exchange with the second vapor phase prior to recovery of the same as a product.

By operating in accordance with the present invention, the recovery of higher boiling constituents is significantly increased, when processing a natural gas, preliminary removal of carbon dioxide is eliminated and the horsepower output of the expander or expanders is significantly increased, as well as other improvements and efficiencies.

BRIEF DESCRIPTION OF THE DRAWING

The single FIGURE of the drawing is a schematic illustration of a natural gas plant which can be employed in the practice of the present invention.

DESCRIPTION OF THE PREFERRED EMBODIMENTS

The operation and advantages of the present invention can best be illustrated by a description with reference to the drawing.

In accordance with the drawing, a normally gaseous feed mixture is introduced to the system through line 10. Normally, the feed mixture would be at essentially atmospheric temperature and at an elevated pressure substantially above atmospheric pressure. To the extent that the feed mixture is thus at atmospheric temperature or is at a temperature lower than that at which it can be effectively fractionally distilled, the feed mixture is passed through heat exchanger 12. In heat exchanger 12, the temperature of the feed mixture is lowered substantially to a temperature which, together with the high pressure, will produce a fluid stream 14 comprising both vapor and liquid phases. In order to attain more efficient fractional distillation, the feed gas mixture passing through line 14 is preferably separated into a vapor phase and a liquid phase in separator 16. The liquid phase is discharged from the bottom of separator 16 through line 18 and at least a part of the vapor phase is discharged from the top of the column through line 20. To the extent that the gas mixture, or specifically the vapor phase thereof, is at a pressure higher than can be conveniently and effectively fractionally distilled in a relatively inexpensive distillation means and/or it is desired to condense additional higher boiling constituents, the vapor phase is passed through expansion section 22 of expander-compressor 24. The expanded vapor phase is then passed through line 26. In order to provide flexibility to handle a variety of feed mixtures, a sidestream of vapor phase may be withdrawn from the top of separator 16 and passed through line 28 where it then is combined in line 30 with the expanded vapor phase passing through line 26.

The feed gas mixture, at a temperature substantially below atmospheric temperature and at a pressure substantially above atmospheric pressure, at which temperature and pressure the feed mixture comprises a vapor phase, which is predominantly lower boiling constituents, and a liquid phase which is predominantly higher boiling constituents is frictionally distilled in column 32. Column 32 in case of a natural gas feed mixture, is commonly referred to as a demethanizer. Column 32 preferably comprises a column having an upper rectifying section 34 and a lower stripping section 36. The feed mixture is introduced to column 32 at an upper intermediate point preferably below the rectifying zone or section 34. Where the feed mixture has been separated into a vapor phase and a liquid phase for efficient fractional distillation it will be separated by introducing the vapor phase from line 30 to an uppermost position, preferably between the rectifying section 34 and a stripping section 36, and the liquid phase passing through line 18 would be introduced at an upper intermediate point below the point of introduction of the vapor phase. Column 32 may be a multi-tray column, a packed column or a combination thereof. Fractional distillation is then carried out in column 32 to produce a second liquid phase which is predominantly lower boiling constituents, in the case of natural gas $C_2$ and lower molecular weight hydrocarbons, which is discharged through line 38 and recovered as a product. Where further separation of the liquid phase higher boiling constituents or $C_2$ and higher molecular weight hydrocarbons is desired or necessary, further conventional separation may be carried out. For example, in the case of an ethane and higher molecular weight hydrocarbon product, the ethane would normally be removed by another fractional distillation step in a "deethanizer" column to thereby produce a vapor phase of substantially pure $C_2$ and a liquid phase predominating in $C_3$ and higher molecular weight hydrocarbons. In the same manner, the $C_3$ may be separated from higher molecular weight hydrocarbons, the $C_4$'s from the $C_5$'s, etc. The $C_5$ and higher molecular weight hydrocarbons will generally not be further separated. The vapor phase from column 32 is withdrawn through line 40. In accordance with the preferred embodiment of the present invention, the vapor phase passing through line 40 is then passed through expander section 42 of expander-compressor 44. Obviously, this decreases the pressure and further decreases the temperature thereby forming an expanded fluid comprising a vapor phase and a liquid phase. The expanded fluid is passed through line 46 to a separator 48. Separator 48 separates the expanded fluid into the said vapor phase, which is discharged through line 50, and the liquid phase, which is discharged through line 52. The liquid phase passing through line 52 then is reintroduced into column 32 as a reflux. Preferably, such introduction is into the rectifying section 34 of column 32. This expansion and refluxing of a liquid portion of the overhead from column 32 has a number of advantages. For example, demethanizers normally operate at pressures of anywhere from about 50 to about 450 psia. With conventional systems which include a single or two series expanders ahead the of fractionization zone, the operating pressure of the demethanizer is generally in the lower portion of the above-mentioned range. However, when operating in accordance with the present invention, the demethanizer can be operated at a higher pressure, namely in the higher portion of the above-mentioned range. The system also provides further cooling by such expansion to provide sub-cooled reflux to the fractionator, thus also improving efficiency of separation. The system also permits the processing of feed gases containing relatively high $CO_2$ contents without pretreatment to remove the $CO_2$ from the gas prior to processing. In addition, by operating in accordance with the present system, the horsepower output of the expander 42 and/or the expander 22 is significantly increased over systems in which a single expander or two expanders in series are utilized ahead of the fractional distillation column.

The vapor phase passing through line 50 is passed in indirect heat exchange through heat exchanger 12 in order to cool the feed gas. This, of course, recovers the cold from the vapor phase stream, thereby contributing to the energy efficiency of the system. Obviously, the vapor stream is also warmed by the heat exchange and after heat exchange, this stream will generally be in a gaseous state and is passed through line 54. After utilizing the low boiling constituent stream, or in this case, the methane stream, as a cooling medium, the methane stream can be utilized, at least in part, as an in plant fuel or as sale gas, thus being transmitted to a natural gas pipeline. In the latter instance it is generally necessary to again increase the pressure of the methane stream for transmission. This is accomplished, in accordance with the present invention, by passing at least a part of the methane stream through compression section 56 of expander-compressor 24 and/or compression section 58 of expander-compressor 44. Serially, the gas from line 54 would pass through line 60 to compressor section 56, through line 62 and line 64 to compression section 58 and thence through line 66 where it may be recovered as a pipeline gas through line 68. Inplant fuel may be recovered, without compression, for other purposes through line 70.

In order to fractionally distill the feed mixture in column 32, the lower portion of the column is preferably heated in some fashion. This can be accomplished in several ways. Specifically, a reboiler system is provided by withdrawing a sidestream adjacent the bottom of column 32 through line 72, passing the same through main reboiler section 74 of reboiler 76 and thence returning the sidestream through line 78 to the bottom of column 32 at a point below the point of withdrawal of the sidestream. Preferably, also, a second sidestream is withdrawn from column 32 at a lower intermediate point through line 80, passed through side reboiler section 82 of reboiler 76 and thence back to column 32 through line 84, where it is reintroduced into the column at a point below the point of withdrawal of the second sidestream. Alternatively, the side reboiler can be supplied with a portion of the feed mixture, preferably a portion of the liquid phase passing through line 18, by passing the same through line 86 through side reboiler section 82 and thence back to line 18 through line 88. The first sidestream withdrawn through line 72 and passed through main reboiler section 74 can be further heated in an appropriate trim reboiler 90. After passing through trim reboiler 90, the first sidestream is then reintroduced into column 32 through line 92. Trim reboiler 92 may be supplied with a part of the methane gas stream through line 94. Reboiler 76 is preferably supplied with heat by withdrawing a portion of uncooled feed gas through line 96 and passing the same through reboiler 76 and line 98 back to the main gas stream flowing through line 14. The point of reintroduction of this portion of the feed gas into the main gas stream would, of course, depend upon its temperature. In the instance illustrated, the temperature of this portion of the feed gas has been reduced in reboiler 76 to a temperature at which it can be combined with the cooled gas discharged from heat exchanger 12. The volume of feed gas utilized in reboiler 76 can be controlled by measuring the temperature of the methane stream after it passes through heat exchanger 12 and the temperature of the feed gas and controlling the volume of feed gas through line 96 in accordance with a predetermined difference in the measured temperatures.

Depending upon the pressure and character of the feed gas, a portion thereof may also be bypassed around the natural gas plant through line 100 and withdrawn as a product for pipeline gas through line 68 or fuel through line 70. The volume of gas withdrawn through line 100 can be appropriately controlled by a pressure indicator-controller.

The system, as described up to this point, has been described for the processing of a lean gas stream, that is, one having a comparatively low concentration of $C_2$ and higher hydrocarbons. However, the system may also be utilized to process rich gas streams, that is, those having high concentrations of $C_2$ and higher hydrocarbons. This is illustrated by the alternative cooling illustrated as in the FIGURE. Specifically, the feed gas passes consecutively through heat exchanger 102, propane cooler 14 and heat exchanger 106. Appropriately, the vapor phase passing through line 50 is passed in indirect heat exchange with the feed gas by passing the same serially through heat exchanger 106 and heat exchanger 102.

The following example further illustrates the operation of the system of the present invention.

Table 1, below, sets forth constituents of a specific illustrative gas stream. Specifically, in Table 1, the composition of the natural gas is illustrated in terms of mole% of each component and moles per day throughput. A computer simulation of the processing of this gas in the system illustrated in the FIGURE is also listed in Table 1 which shows the composition of the $C_2$ product (DeC$_1$ product), the pipeline gas and/or fuel product (residue gas) and the liquid reflux stream to the fractionization zone (DeC$_1$ reflux stream), all in moles per day.

TABLE I

| Comp. | Description M.W. | Description G/Mol | Mol % Inlet Gas (10) | Inlet Gas to Exp. Plant (10) | DeC, Product (38) | Residue Gas (68-70) | DeC, Reflux Stream (52) | Recovery % |
|---|---|---|---|---|---|---|---|---|
| $N_2$ | 28.02 |  | 0.2 | 626 | — | 626 | 5.5 |  |
| $CO_2$ | 44.01 | 6.38 | 0.6 | 1,878 | 911 | 967 | 261 |  |
| $H_2S$ | 34.08 | 5.17 | — | — | — | — | — |  |
| $C_1$ | 16.04 | 6.40 | 94.1 | 272,895 | 142 | 272,753 | 11,823 |  |
| $C_2$ | 30.07 | 10.12 | 3.1 | 8,850 | 7575 | 1,275 | 1170.5 | 85.6 |
| $C_3$ | 44.09 | 10.42 | 1.0 | 3,038 | 3038 | — | 2.0 | 100 |
| $IC_4$ | 58.12 | 12.38 |  | 875 | 875 | — | — | 100 |
| $nC_4$ | 58.12 | 11.93 |  | 635 | 635 | — | — | 100 |
| $IC_5$ | 72.15 | 13.85 | 0.9 | 290 | 290 | — | — | 100 |
| $nC_5$ | 72.15 | 13.71 |  | 186 | 186 | — | — | 100 |
| $C_6$ | 86.17 | 15.57 |  | 299 | 299 | — | — | 100 |
| $C_7$ | 100.20 | 17.46 |  | 290 | 290 | — | — | 100 |
| Totals |  |  |  | 289,860 | 14,240 | 275,620 | 13,262 |  |

Table 1 also sets forth the recovery of $C_2$ or ethane and the recovery of $C_3$ and higher molecular weight hydrocarbons by such an operation. It is to be seen that, by operating in accordance with the present invention, 85.6% of the original ethane can be recovered from the natural gas and 100% of the propane and higher molecular weight hydrocarbons. A comparative computer simulation utilizing the same gas composition in a conventional process, having one expansion stage ahead of the fractionization zone, resulted in about 65% ethane recovery and about 95.7% propane and higher molecular weight hydrocarbon recovery. The numerals in parenthesis in Table 1 illustrate the feed lines through which the particular stream flows.

By way of further illustration, typical conditions for the operation of the process on a gas such as that set forth above, are listed below. The inlet gas or feed gas through line 10 would have a pressure of about 715 psig and a temperature of about 75° F. Separator 16 would be operated at a pressure of about 705 psig and −94° F. The demethanizer column 32 would be operated at a pressure of about 325 psig, a temperature at the top or in the rectifying zone of about −146° F. and a temperature at the bottom, i.e. the bottom of the stripping section, of about 55° F. The generator 48 would be operated at a pressure of about 225 psig and a temperature of about −164° F. The product liquid discharged through line 38 would be at a pressure of about 370 psig at a temperature of about 60° F. Finally, the pipeline gas recovered through line 68 would be at a pressure of about 277 psig and a temperature of about 106° F.

While specific materials, specific modes of operation, specific equipment and specific conditions of operation have been set forth herein by way of illustration, it is to be recognized that such specific recitals are by way of illustration only and to set forth the best mode of operation of the present invention and are not to be considered limiting.

That which is claimed:

1. A method for separating ethane and higher molecular weight hydrocarbons from a natural gas feed, predominating in methane and containing significant amounts of ethane and higher molecular weight hydrocarbons and carbon dioxide, having a first pressure substantially above atmospheric pressure and a first temperature substantially below atmospheric temperature and at which first pressure and first temperature said feed comprises both vapor and liquid phases, comprising:

(a) separating said feed, in a separation zone, to separate the vapor phase of said feed, as a first vapor phase, and the liquid phase of said feed, as a first liquid phase;

(b) expanding at least a part of said first vapor phase to reduce the pressure thereof to a second lower pressure and reduce the temperature thereof to a second lower temperature and produce a first expanded fluid stream;

(c) fractionally distilling said first expanded fluid stream, any unexpanded remaining portion of said first vapor phase and said first liquid phase, in a fractionation zone, to produce a second vapor phase, significantly enriched in methane and carbon dioxide, and a second liquid phase, predominating in ethane and higher molecular weight hydrocarbons and containing insignificant amounts of methane;

(d) expanding at least a portion of said second vapor phase to reduce the pressure thereof to a third lower pressure and reduce the temperature thereof to a third lower temperature and produce a second expanded fluid stream, as a third vapor phase, predominating in methane, significantly enriched in carbon dioxide and containing insignificant amounts of ethane in higher molecular weight hydrocarbons, and a third liquid phase;

(e) separating said second expanded fluid stream, in a separation zone, to separate said third vapor phase and said third liquid phase;

(f) recycling said third liquid phase to said fractionation zone, as a reflux;

(g) recovering said third vapor phase as a product; and (h) recovering said second liquid phase as a product;

(i) maintaining the temperature and pressure at all times throughout the process substantially within the liquid range of carbon dioxide.

2. A method in accordance with claim 1 wherein the pressure of the third vapor phase is controlled by withdrawing a portion of the feed, in accordance with the pressure of said feed, and adding thus withdrawn portion of the feed to the product third vapor phase.

3. A method in accordance with claim 1 wherein the fractionation zone comprises and upper rectifying section and a lower stripping section.

4. A method in accordance with claim 3 wherein the feed is introduced into the fractionation zone at a point at least as low as the top of the stripping section and the third liquid phase is recycled to the rectifying section of said fractionation zone.

5. A method in accordance with claim 3 wherein the expanded portion of the first vapor phase and any unexpanded remaining portion of the first vapor phase is introduced to the fractionation zone between the rectifying section and the stripping section and the first liquid phase is introduced into the upper portion of said stripping section below the point of introduction of said expanded frist vapor phase and any unexpanded remaining portion of said first vapor phase.

6. A method in accordance with claim 1 wherein the volume of the first vapor phase thus expanded is controlled in accordance with the pressure of said first vapor phase.

7. A method in accordance with claim 1 wherein the volume of the second vapor phase thus expanded is controlled in accordance with he pressure of said second vapor phase.

8. A method in accordance with claim 1 wherein the bottom of the fractionation zone is heated, at least in part, by withdrawing a side stream adjacent the bottom of said fractionation zone, passing the thus withdrawn side stream in indirect heat exchange with a portion of the feed and returning the thus withdrawn and heated side stream to said fractionation zone at a point below the point of withdrawal.

9. A method in accordance with claim 8 wherein the volume of the feed thus heat exchanged with the side stream withdrawn from the fractionation zone is controlled in accordance with the temperature of said feed.

10. A method in accordance with claim 1 or 8 wherein a lower intermediate portion of the fractionation zone is heated, at least in part, by withdrawing a second side stream from said lower intermediate portion of said fractionation zone, passing the thus withdrawn second side stream in indirect heat exchange with a portion of the feed and returning the thus withdrawn and heated second side stream to said lower intermediate portion of said fractionation zone at a point below the point of withdrawal.

11. A method in accordance with claim 1 or 8 wherein a portion of the first liquid phase is heated prior to fractionally distilling the same by withdrawing a portion of said first liquid phase, passing the thus withdrawn portion of said first liquid phase in indirect heat exchange with a portion of said feed and passing the thus withdrawn and heated portion of said first liquid phase to the fractionation zone.

12. A method in accordance with claim 1 wherein at least a portion of the first vapor phase is thus expanded by passing the same through a first expansion section of a first expander-compressor, the compression section of said first expander-compressor is driven by said first expansion section, the third vapor phase is thus expanded by passing the same through a second expansion section of a second expander-compressor, the second compression section of said second expander-compressor is driven by said second expansion section and at least a part of the fourth vapor phase is compressed in at least one of said first compression section and said second compression section.

13. A method for separating ethane and higher molecular weight hydrocarbons from a natural gas feed, predominating in methane and containing significant amounts of ethane and higher molecular weight hydrocarbons and carbon dioxide, having a first pressure substantially above atmospheric pressure and a first temperature near atmospheric temperature, comprising:

(a) cooling said feed to reduce the temperature thereof to a second lower temperature substantially below atmospheric temperature and at which first pressure and second temperature said feed comprises both vapor and liquid phases;

(b) separating the thus cooled feed, in a separation zone, to separate the vapor phase of said feed, as a first vapor phase, and the liquid phase of said feed, as a first liquid phase;

(c) expanding at least a portion of said first vapor phase to reduce the pressure thereof to a second lower pressure and reduce the temperature thereof to a third lower temperature and produce a first expanded fluid stream;

(d) fractionally distilling said first expanded fluid stream, any unexpanded remaining portion of said first vapor phase and said first liquid phase, in a fractionation zone, to produce a second vapor phase, significantly enriched in methane and carbon dioxide, and a second liquid phase, predominating in ethane and higher molecular weight hydrocarbons and containing insignificant amounts of methane;

(e) expanding at least a portion of said second vapor phase to reduce the pressure thereof to a third lower pressure and reduce the temperature thereof to a fourth lower temperature and produce a second expanded fluid stream, as a third vapor phase, predominating in methane, significantly enriched in carbon dioxide and containing insignificant amounts of ethane and higher molecular weight hydrocarbons, and a third liquid phase;

(f) separating said second expanded fluid stream, in a separation zone, to separate said third vapor phase and said third liquid phase;

(g) recycling said third vapor phase to said fractionation zone, as a reflux;

(h) recovering said third vapor phase as a product; and (i) recovering said second liquid phase as a product;

(j) maintaining the temperature and pressure at all times throughout the process substantially within the liquid range of carbon dioxide.

14. A method in accordance with claim 13 wherein the pressure of the third vapor phase is controlled by withdrawing a portion of the feed and adding the thus withdrawn portion of the feed to said third vapor phase in accordance with the pressure of said feed.

15. A method in accordance with claim 13 wherein the fractionation zone comprises an upper rectifying section and a lower stripping section.

16. A method in accordance with claim 15 wherein the feed is introduced into the fractionation zone at a point at least as low as the top of the stripping section and the third liquid phase is recycled to the rectifying section of the fractionation zone.

17. A method in accordance with claim 15 wherein the expanded first vapor phase of the feed and the unexpanded remaining portion of the first vapor phase of the feed is introduced to the fractionation zone between the rectifying section and the stripping section and the first liquid phase of the feed is introduced into the upper portion of the stripping section below the point of introduction of said expanded first vapor phase and said unexpanded remaining portion of said first vapor phase.

18. A method in accordance with claim 13 wherein the volume of the first vapor phase thus expanded is controlled in accordance with the pressure of said first vapor phase.

19. A method in accordance with claim 13 wherein the volume of the second vapor phase thus expanded is controlled in accordance with the pressure of said second vapor phase.

20. A method in accordance with claim 13 wherein the bottom of the fractionation zone is heated, at least in part, by withdrawing a side stream adjacent the bottom of said fractionation zone, passing the thus withdrawn side stream in indirect heat exchange with an uncooled portion of the feed and returning the thus withdrawn and heated side stream to the fractionation zone at a point below the point of withdrawal.

21. A method in accordance with claim 13 or 20 wherein a lower intermediate portion of the fractionation zone is heated, at least in part, by withdrawing a second side stream from said lower intermediate portion of said fractionation zone, passing the thus withdrawn second side stream in indirect heat exchange with an uncooled portion of the feed and returning the thus withdrawn and heated second side stream to said lower intermediate portion of said fractionation zone at a point below the point of withdrawal.

22. A method in accordance with claim 20 wherein the volume of feed thus used to heat the side stream from the fractionation zone is controlled in accordance with the temperature of said feed.

23. A method in accordance with claim 13 or 20 wherein a portion of the first liquid phase is heated prior to fractionally distilling the same by withdrawing a portion of said first liquid phase, passing the thus withdrawn portion of said first liquid phase in indirect heat exchange with an uncooled portion of said feed and passing the thus withdrawn and heated portion of said first liquid phase to the fractionation zone.

24. A method in accordance with claim 13 wherein the at least a portion of the first vapor phase is thus expanded by passing the same through a first expansion section of a first expander-compressor, the compression section of said first expander-compressor is driven by said first expansion section, the third vapor phase is thus expanded by passing the same through a second expansion section of a second expander-compressor, the second compression section of said second expander-compressor is driven by said second expansion section and at least part of the fourth vapor phase is compressed in at least one of said first compression section and said second compression section.

25. A method in accordance with claim 13 wherein the feed is cooled, at least in part, by indirect heat exchange with at least a portion of the third vapor phase.

* * * * *